United States Patent [19]

Poittevin et al.

[11] 4,001,447
[45] Jan. 4, 1977

[54] 2-HYDROXYMETHYL-THIAZOLE-5-CARBOXYLIC ACID DERIVATIVES

[75] Inventors: André Poittevin, Vaires-sur-Marne; Michel Hardy, Maisons-Alfort, both of France

[73] Assignee: Roussel Uclaf, Paris, France

[22] Filed: Oct. 15, 1975

[21] Appl. No.: 622,635

[30] Foreign Application Priority Data

Oct. 29, 1974  France ............................. 74.36080

[52] U.S. Cl. ................................. 424/270; 260/299; 260/302 R
[51] Int. Cl.² ..................................... C07D 277/34
[58] Field of Search ...................... 260/302 R, 299; 424/270

[56] References Cited
UNITED STATES PATENTS 3,897,441  7/1975  Edwards ........................ 260/302 R

*Primary Examiner*—R. J. Gallagher
*Attorney, Agent, or Firm*—Hammond & Littell

[57] ABSTRACT

Novel 2-hydroxymethyl-thiazole-5-carboxylic acid derivatives of the formula

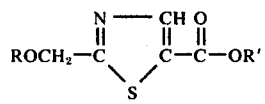

wherein R is selected from the group consisting of hydrogen, alkyl of 1 to 4 carbon atoms, alkylcarbonyl of 2 to 5 carbon atoms, benzoyl, phenyl optionally substituted with at least one halogen and

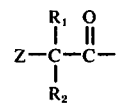

$R_1$ and $R_2$ are individually selected from the group consisting of hydrogen and alkyl of 1 to 3 carbon atoms, Z is selected from the group of phenyl and phenoxy optionally substituted with at least one halogen and R' is selected from the group consisting of hydrogen and alkyl of 1 to 4 carbon atoms and alkali metals, alkaline earth metals and aluminum salts, having a marked hypolipemiant activity as well as a clear vasodilatatory activity and which may possess hypocholesterolemiant activity and their preparation.

20 Claims, No Drawings

2-HYDROXYMETHYL-THIAZOLE-5-CARBOXYLIC ACID DERIVATIVES

STATE OF THE ART

Commonly assigned U.S. Pat. No. 3,882,110 discloses thiazole-5-carboxylic acid compounds substituted in the 2-position with a linear alkyl group of 1 to 12 carbon atoms having hypolipemiant activity.

OBJECTS OF THE INVENTION

It is an object of the invention to provide the novel 2-hydroxymethyl-thiazole-5-carboxylic acid compounds of formula I as well as novel processes for their preparation.

It is another object of the invention to provide novel hypolipemiant, vasodilatatory and, some of them hypocholesterolemiant, compositions.

It is an additional object of the invention to provide a novel method of reducing the amount of sanguine lipids in warm-blooded animals.

These and other objects and advantages of the invention will become obvious from the following detailed description.

THE INVENTION

The novel products of the invention have the formula

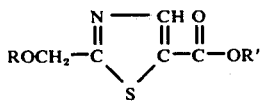   I wherein R is selected from the group consisting of hydrogen, alkyl of 1 to 4 carbon atoms, alkylcarbonyl of 2 to 5 carbon atoms, benzoyl, phenyl optionally substituted with at least one halogen and

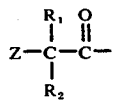

$R_1$ and $R_2$ are individually selected from the group consisting of hydrogen and alkyl of 1 to 3 carbon atoms, Z is selected from the group of phenyl and phenoxy optionally substituted with at least one halogen and R' is selected from the group consisting of hydrogen and alkyl of 1 to 4 carbon atoms and alkali metals, alkaline earth metals and aluminum salts.

Among the compounds of formula I, alkyl of 1 to 4 carbon atoms includes methyl, ethyl, n-propyl, isopropyl, n-butyl, isobutyl and tert.-butyl. While R and Z may be phenyl substituted with one or more halogens such as fluorine, chlorine, or bromine, they preferably are phenyl with chlorine in the o-, m- or p- position.

Among the preferred compounds of formula I are those wherein R is hydrogen, alkyl of 1 to 4 carbon atoms, alkylcarbonyl of 2 to 5 carbon atoms, benzoyl, halophenyl or

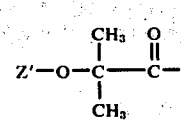

wherein Z' is phenyl substituted with at least one halogen and R' is defined as above and their alkali metal, alkaline earth metal and aluminum salts when R' is hydrogen. Other preferred compounds of formula I are those wherein R is hydrogen, methyl, acetyl, benzoyl p-chlorophenyl or

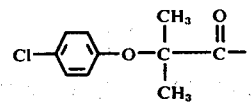

and R' has the above definition. Preferably, R is hydrogen.

A process for the production of the compounds of formula I comprises reacting a compound of the formula

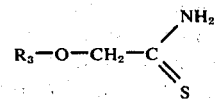   II wherein $R_3$ is alkyl of 1 to 4 carbon atoms, alkylcarbonyl of 2 to 5 carbon atoms, benzoyl or phenyl optionally substituted with at least one halogen with a compound of the formula

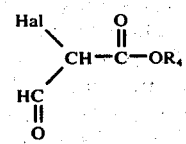   III wherein Hal is a halogen and $R_4$ is alkyl of 1 to 4 carbon atoms to form a compound of the formula

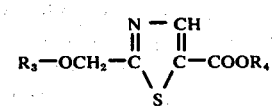   IV wherein R is $R_3$ and R' is $R_4$, which compound, if $R_3$ is alkyl of 1 to 4 carbon atoms or phenyl optionally substituted with at least one halogen may be saponified to obtain the corresponding compound of formula I wherein R' is hydrogen. If $R_3$ is alkylcarbonyl of 2 to 5 carbon atoms or benzoyl, the compound of formula IV may be saponified to obtain a compound of the formula

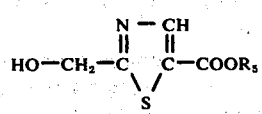   V wherein $R_5$ is hydrogen or alkyl of 1 to 4 carbon atoms which is a compound of formula I in which R is hydrogen and R' is $R_5$ and if desired, the latter product may be reacted with a compound of the formula

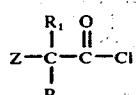   VI to obtain a compound of the formula

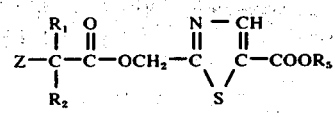   VII which is a compound of formula I wherein R is

and R' is $R_5$.

The reaction between the compounds of formulae II and III is preferably effected in an organic solvent such as dichloroethane, benzene, toluene, dioxane, cyclohexane, ether or tetrahydrofuran. The saponification of the compound of formula IV wherein $R_3$ is alkyl of 1 to 4 carbon atoms or phenyl optionally substituted with at least one halogen is effected with a strong base in an organic solvent such as methanol, ethanol, propanol, isopropanol, butanol, benzene, toluene, or cyclohexane, preferably at reflux.

The saponification of a compound of formula IV wherein $R_3$ is benzoyl or alkylcarbonyl of 2 to 5 carbon atoms is preferably effected with heat and a strong alkaline base to form the compound of formula V wherein $R_5$ is hydrogen. To form a compound of formula V wherein $R_5$ is alkyl of 1 to 4 carbon atoms, the saponification is effected with a strong alkaline base at room temperature. The said saponifications are effected in an organic solvent such as the first saponification.

The reaction of compounds of formulae V and VI is preferably effected in an organic solvent such as tetrahydrofuran, benzene, toluene, or cyclohexane and in the presence of an organic base such a pyridine, diethylamine, triethylamine or triethanolamine.

The salts of the compounds of formula I wherein R' is alkali metal, alkaline earth metal or aluminum are prepared by reaction of the acid with the corresponding mineral base. The reaction is preferably effected in a solvent or mixture of solvents such as water, ether, ethanol or acetone.

The compounds of formula II may be prepared by various methods described in the literature such as J. Org. Chem., Vol. 15 (1950), p. 694–699; Helvetica Chimica Acta, Vol. 3 (1948), p. 652; and Beilstein, 4e supp., Vol. 9, p. 856.

The novel hypolipemiant compositions of the invention are comprised of an effective amount of at least one compound of formula I and a pharmaceutical carrier. The compositions may be in the form of tablets, dragees, gelules, granules, suppositories or injectable solutions or suspensions prepared in the usual fashion.

The compositions are very useful in the treatment of acute or chronic hyperlipemia, coronary insufficiency, cardiac insufficiencies of atheromatosis origin, chronic anginic states or hypercholesterolemia.

The compositions may be prepared by incorporating the active compounds into the usual excipients such as talc, arabic gum, lactose, starch, magnesium stearate, cocoa butter, aqueous or non-aqueous vehicles, fatty bodies of animal or vegetable origin, paraffinic derivatives, glycols, preservatives and/or diverse wetting agents, dispersants or emulsifiers.

The novel method of the invention for reducing the amount of sanguine lipids in warm-blooded animals comprises administering to warm-blooded animals an effective amount of at least one compound of formula I. The compounds may be administered orally, rectally or parenterally. The usual daily does is 2 to 50 mg/kg depending upon the specific product and method of administration.

In the following examples there are described several preferred embodiments to illustrate the invention. However, it should be understood that the invention is not intended to be limited to the specific embodiments.

EXAMPLE 1 ethyl 2-benzoyloxymethyl-thiazole-5-carboxylate

A mixture of 9.14 g of 2-benzoyloxythioacetamide, 9 g of ethyl α-formyl-chloroacetate and 100 ml of dichloroethane was refluxed for 4 hours and after the addition of 4.5 g of ethyl β-formyl-chloroacetate, reflux was maintained for 2 hours. The mixture was cooled and was washed first with aqueous sodium carbonate and then water. The mixture was dried and the solvent was evaporated to obtain 14 g of raw product which was chromatographed over silica gel. Elution with a benzene-ethyl acetate mixture yielded 12.5 g of ethyl 2-benzoyloxymethyl-thiazole-5-carboxylate in the form of an oil.

EXAMPLE 2

2-hydroxymethyl-thiazole-5 -carboxylic acid

A mixture of 13.5 g of ethyl 2-benzoyloxymethyl-thiazole-5-carboxylate, 135 ml of water and 8 ml of postassium hydroxide was heated at 95° C with stirring for an hour and the mixture was cooled and extracted with ether. The aqueous phase was acidified and was then saturated with sodium chloride. The mixture was extracted with ethyl acetate and the organic extracts were washed with water, dried and evaporated to dryness to obtain 11,5 g of raw product. The product was chromatographed over silica gel and was eluted with a 8–2 methylene chloride-ethanol mixture containing 2% acetic acid. The 6 g of product were crystallized from a 3–1 acetone-methanol mixture to obtain 5.04 g of 2-hydroxymethyl-thiazole -5-carboxylic acid melting at 193° C.

Analysis: $C_5H_5O_3NS$;

Calculated: %C 37.73 %H 3.16 %N 8.80 %S 20.14;
Found: 37.8 3.3 8.8 20.3.

EXAMPLE 3

2-[α-(p-chlorophenoxy)-α,α-dimethylacetoxymethyl]-thiazole

-5-carboxylic acid 14.7 g of p-chlorophenoxy-isobutyric acid chloride and 50 ml of tetrahydrofuran were added with stirring to a mixture of 9.5 g of 2-hydroxymethyl-thiazole-5-carboxylic acid, 160 ml of tetrahydrofuran and 8 ml of pyridine and the mixture was refluxed for 3 hours and then cooled to room temperature. The mixture was filtered and the filtrate was evaporated to dryness under reduced pressure to obtain 28 g of raw product. The product was dissolved in 500 ml of water and 20 ml of triethylamine and the solution was extracted with ethyl acetate. The aqueous phase was acidified with acetic acid and was then extracted with methylene chloride. The organic extracts were washed with water, dried and concentrated to dryness. The oil residue was taken up in 500 ml of isopropyl ether at 40° C and the solution was filtered. The filtrate was concentrated to obtain 16 g of crystalline product. The latter was taken up in cyclohexane and vacuum filtered and the precipitate was crystallized from benzene to obtain 4.8 g of 2-[α-(p-chlorophenoxy)-α,α-dimethyl-acetoxymethyl]-thiazole -5-carboxylic acid melting at 124° C.

Analysis: $C_{15}H_{14}ClNO_5S$;

Calculated %C 50.64 %H 3.97 %N 3.94 %Cl 9.96 %S 9.01;

Found: 50.5 3.9 3.9 9.9 9.3.

EXAMPLE 4 methyl 2-[α-(p-chlorophenoxy)-α,α-dimethylacetoxymethyl]-thiazole-5-carboxylate

STEP A: methyl 2-hydroxymethyl-thiazole-5-carboxylate

Using the procedure of Example 1, 2and methyl α-formyl-chloroacetate were reacted to form methyl 2-benzoyloxymethyl-thiazole-5A mixture of the said product, potassium hydroxide and methanol stood at room temperature for an hour and was then evaporated to dryness. The residue was taken up in water and the mixture was acidified with concentrated hydrochloric acid and was extracted with methylene chloride. The organic extracts were washed, dried and evaporated to dryness under reduced pressure. The product war purified by crystallization from isopropyl ether to obtain methyl 2-hydroxymethyl-thiazole-5-carboxylate.

STEP B: methyl 2-[α-(p-chlorophenoxy)-α,α-dimethylacetoxymehtyl]-thiazole-5-carboxylate Using the procedure of Example 3, methyl 2-hydroxymethyl-thiazole-5-carboxylate and p-chlorophenoxyisobutyric acid chloride were reacted in toluene and triethylamine to obtain methyl 2-[α-(p-chlorophenoxy)-α,α-dimethylacetoxymethyl]-thiazole-5-carboxylate melting at 80° C.

Analysis: $C_{16}H_{16}ClNO_5S$;

Calculated %C 51.96 %H 4.36 %N 3.79 %Cl 9.59 %S 8.67;

Found: 51.9 4.3 3.6 9.4 8.8.

EXAMPLE 5

25-carboxylic acid

STEP A: ethyl 2-(chlorophenoxymethyl)-thiazole-5-carboxylate

A mixture of 10.4 g of p-chlorophenoxy thioacetamide, 7.65 g of ethyl α-formyl-chloroacetate and 104 ml of dichloroethane was refluxed for 2 ½hours and after the addition of 3.18 g of ethyl α-formyl-chloroacetate, the mixture was refluxed for another 4 hours. The mixture was cooled and was washed with an aqueous sodium carbonate solution and then with water and was dried to obtain 15.5 g of raw product. The latter was chromatographed over silica gel and was eluted with a benzene-ethyl acetate mixture to obtain 10.9 g of 2-(p-chlorophenoxymethyl)-thiazole-5-carboxylate melting at 70° C.

STEP B: 2-(p-chlorophenoxymethyl)-thiazole-5-carboxylic acid

A mixture of 10.9 of ethyl 2-(p-chlorophenoxymethyl)-thiazole-5-carboxylate, 165 ml of methanol, 10 ml of postassium hydroxide and 20 ml of water was refluxed for 30 minutes and was then cooled and extracted with ethyl acetate. The aqueous phase was acidified and 2-(p-chlorophenoxymethyl)-thiazole-5-carboxylic acid was extracted with ethyl acetate and then a mixture of chloroform-methanol. The combined extracts were dried and evaporated to dryness to obtain 7.9 g of a crystalline residue. The residue was crystallized from isopropanol to obtain 6.92 g of the desired acid and the latter in the form of its triethylamine salt was chromatographed over silica gel. Elution with first a 1-1 chloroform-ethyl acetate mixture and then a 90-10-1 methylene chloride-ethyl acetate-acetic acid mixture gave 6.7 g of raw product. The latter was purified by sublimation at 190° C under reduced pressure and was crystallized from isopropanol containing 10% water to obtain 5.23 g of 2-(p-chlorophenoxymethyl)-thiazole--carboxylic acid melting at 215° C.

Analysis: $C_{11}H_8O_3NSCl$;

Calculated: %C 48.98 %H 2.98 %N 5.19 %S 11.88 %Cl 13.14;

Found: 49.0 3.0 5.3 12.0 13.1.

EXAMPLE 6

2-methoxymethyl-thiazole-5-carboxylic acid

STEP A: ethyl 2-methoxymethyl-thiazole-5-carboxylate

A mixture of 12.61 g of 2-methoxy-thioacetamide and 150 ml dichloroethane was heated to distill off 10 ml of solvent and after the addition of 18 g ethyl α-formyl-chloroacetate, the mixture was refluxed for 3 hours. 5.7 g of ethyl chloroformyl acetate were added and the mixture was refluxed for 2 more hours and was then cooled. The mixture was washed with a sodium bicarbonate solution and then with water, was dried and evaporated to dryness to obtain 27.6 g of raw product. The latter was chromatographed over silica gel and was eluted with an 8-2 benzene-ethyl acetate mixture to obtain 22.5 g of ethyl 2-methoxymethyl-thiazole-5-carboxylate.

STEP B: 2-methoxymethyl-thiazole-5-carboxylic acid

A mixture of 21 g of ethyl 2-methoxymethyl-thiazole -5-carboxylate, 100 ml of methanol, 25 ml of potassium hydroxide solution and 25 ml of water was refluxed for 40 minutes and was then cooled and diluted with water. The mixture was extracted with methylene chloride and the aqueous phase was acidified with hydrochloric acid. The aqueous phase was then extracted with chloroform and the organic extracts were dried and evaporated to dryness to obtain 18 g of crystals. The latter was dissolved in 50 ml of methylene chloride and 5 ml of triethylamine and the solution was chromatographed over silica gel. Successive elutions with methylene chloride and then with a 1-1 benzene-ethyl acetate mixture containing 3% acetic acid yielded a product which was crystallized from ether, then isopropyl ether to obtain 14.08 g of 2-methoxymethyl-thiazole-5-carboxylic acid melting at 131° C.

Analysis: $C_6H_7O_3NS$;
Calculated: %C 41.61 %H 4.07 %N 8.08 %S 18.51;
Found: 41.8 4.1 7.9 18.3.

EXAMPLE 7

Tablets were prepared consisting of 25 mg of 2-hydroxymethyl-thiazole-5-carboxylic acid or methyl 2-[α-(p-chlorophenoxy)-α,α-dimethylacetoxymethyl]-thiazole-5-carboxylate and an excipient of lactose, starch, talc and magnesium stearate to have a final tablet weight of 500 mg.

PHARMACOLOGICAL STUDY

A. Acute toxicity

The acute toxicity was determined in lots of 10 mice weighing 18 to 22 g and the poroducts were administered intraperitoneally as a suspension in carboxymethyl cellulose. The animals were observed for a week to determine the $DL_{50}$ dose and the results are reported in Table I.

B. Hypolipemiant Activity

Male rats of the Sprague Dawley S.P.F. strain weighing about 180 to 200 g were not fed for 24 hours and then received the test products orally. One hour later, the animals were killed for carotidiene section and samples of the blood were taken to determine the effect of the dosage on free fatty acids in the blood.

The extraction of the free fatty acids was determined by the technique of Dole [J. Clin. Invest., Vol. 38 (1959), p. 1544-1554]as modified by Trout et al [J. Lipid. Res., Vol. 1 (1960), p. 199–202]. The plasmatic extract free of phospholipids was determined colorimetrically by the method of Anthonis [J. Lipid. Res., Vol. 6 (1965), p. 307–312]and the $DA_{50}$, dose which diminished the free fatty acid by 50% as compared to the controls is reported in Table I.

TABLE I

| Product | $DL_{50}$ mg/kg | $DA_{50}$ mg/kg |
|---|---|---|
| 2-hydroxymethyl-thiazole-5-carboxylic acid | ≅ 350 | 1.5 |
| 2-[α-(p-chlorophenoxy)-α,α-dimethylacetoxymethyl]-thiazole-5-carboxylic acid | 350 | ~ 30 |
| methyl 2-[α-(p-chlorophenoxy)-α,α-dimethylacetoxymethyl]-thiazole-5-carboxylate | > 1000 | ≅ 7 |
| 2-methoxymethyl-thiazole-5-carboxylic acid | 300 | ~ 50 |
| 2-(p-chlorophenoxymethyl)-thiazole-5-carboxylic acid | 400 | — |

C. Peripheric vasodilatatory activity

The peripheric vasodilatatory activity was determined on albino guinea pigs which manifestations appeared as a reddening of the ears after a certain time of latency. The animals were fasted and the test product was administered orally. The time for the appearance of the reddening of the ears and its duration and intensity were subjectively determined on a scale of 1 to 3 and the results are reported in Table II.

TABLE II

| Product | Dose in mg/kg | Latency in min. | Duration in min. | Intensity |
|---|---|---|---|---|
| 2-hydroxymethyl-thiazole-5-carboxylic acid | 20 | 29 | 40 | 2.4 |

The vasodilatatory activity was manifested at greater doses more elevated than the hypolipemiant activity and it did not appear until after a sufficiently important latency time.

Various modifications of the compounds and processes of the invention may be made without departing from the spirit or scope thereof and it is to be understood that the invention is to be limited only as defined in the appended claims.

We claim:
1. A compound of the formula

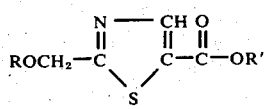

wherein R is selected from the group consisting of hydrogen, alkyl of 1 to 4 carbon atoms, alkylcarbonyl of 2 to 5 carbon atoms, benzoyl, phenyl optionally substituted with at least one halogen and

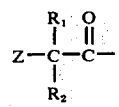

$R_1$ and $R_2$ are individually selected from the group consisting of hydrogen and alkyl of 1 to 3 carbon atoms, Z is selected from the group consisting of phenyl and phenoxy optionally substituted with at least one halogen and R' is selected from the group consisting of hydrogen and alkyl of 1 to 4 carbon atoms and alkali metals, alkaline earth metals and aluminum salts.

2. A compound of claim 1 wherein R is selected from the group consisting of hydrogen, alkyl of 1 to 4 carbon atoms, alkylcarbonyl of 2 to 5 carbon atoms, benzoyl, phenyl substituted with a halogen and

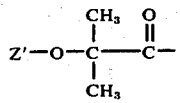

and Z' is phenyl substituted with at least one halogen.

3. A compound of claim 1 wherein R is selected from the group consisting of hydrogen, methyl, acetyl, benzoyl, p-chlorophenyl and

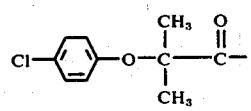

4. A compound of claim 1 wherein R is hydrogen.
5. A compound of claim 1 which is ethyl 2-benzoyloxymethyl-thiazole-5-carboxylate.
6. A compound of claim 1 which is 2-hydroxymethyl-thiazole-5-carboxylic acid.
7. A compound of claim 1 which is 2-[α-(p-chlorophenoxy-α,α-dimethylacetoxymethyl]-thiazole-5-carboxylic acid.
8. A compound of claim 1 which is methyl 2-[α-(p-chlorophenoxy)-α,α--dimethylacetoxymethyl]-thiazole-5-carboxylate.

9. A compound of claim 1 which is 2-(p-chlorophenoxymethyl)-thiazole-5-carboxylic acid.

10. A compound of claim 1 which is 2-methoxymethylthiazole-5-carboxylic acid.

11. A compound of claim 1 which is methyl 2-benzoyloxy-methyl-thiazole-5-carboxylate.

12. A compound of claim 1 which is methyl 2-hydroxymethyl-thiazole-5-carboxylate.

13. A compound of claim 1 which is ethyl 2-(p-chlorophenoxymethyl)-thiazole-5-carboxylate.

14. A compound of claim 1 which is ehtyl 2-methoxymethyl-thiazole-5-carboxylate.

15. A hypolipemiant composition comprising an hypolipemiantly effective amount of at least one compound of claim 1 and an inert pharmaceutical carrier.

16. A method of reducing the amount of sanguine lipids in warm-blooded animals which comprises administering to warm-blooded animals an hypolipemiantly effective amount of at least one compound of claim 1.

17. The method of claim 16 wherein R is selected from the group consisting of hydrogen, alkyl of 1 to 4 carbon atoms, alkylcarbonyl of 2 to 5 carbon atoms, benzoyl, phenyl substituted with a halogen and

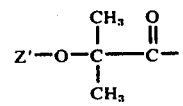

and Z' is phenyl substituted with at least one halogen.

18. The method of claim 16 wherein R is selected from the group consisting of hydrogen, methyl, acetyl, benzoyl, p-chlorophenyl and

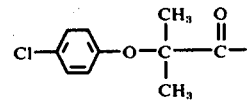

19. The method of claim 16 wherein R is hydrogen.

20. The method of claim 16 wherein the product is 2-hydroxymethyl-thiazole-5-carboxylic acid.

* * * * *